(12) United States Patent
Dixit

(10) Patent No.: US 7,544,481 B1
(45) Date of Patent: Jun. 9, 2009

(54) NUCLEIC ACIDS ENCODING CD40 BINDING PROTEIN

(75) Inventor: Vishva M. Dixit, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 09/224,556

(22) Filed: Dec. 30, 1998

Related U.S. Application Data

(63) Continuation of application No. 08/826,577, filed on Apr. 2, 1997, which is a continuation of application No. 08/404,832, filed on Mar. 13, 1995, now abandoned.

(51) Int. Cl.
*C12N 15/12* (2006.01)
*C12N 15/63* (2006.01)
*C12N 15/85* (2006.01)

(52) U.S. Cl. .................... 435/69.1; 435/320.1; 435/325; 435/252.3; 536/23.5

(58) Field of Classification Search ................ 536/23.5; 435/69.1, 325, 320.1, 252.3
See application file for complete search history.

(56) References Cited

FOREIGN PATENT DOCUMENTS

| EP | 0 555 880 | 8/1993 |
| EP | 0 585 943 | 3/1994 |
| WO | WO 93/08207 | 4/1993 |
| WO | WO 94/04570 | 3/1994 |

OTHER PUBLICATIONS

Rudinger, In "Peptide Hormones" (ed. J. A. Parsons) University Park Press, Baltimore, pp. 1-7, 1976.*
Allen et al., "CD40 ligand gene defects responsible for X-linked hyper-1gM syndrome" *Science* (1993) 259:990-993.
Altschul et al., "Issues in searching molecular sequence databases" *Nature Genet.* (1994) 6:119-129.
Anderson, "Human gene therapy" *Science* (1992) 256:808-813.
Armitage et al., "CD40 ligand is a T cell growth factor" *Eur. J. Immunol.* (1993) 23:2326-2331.
Armitage et al., "Molecular and biological characterization of a murine ligand for CD40" *Nature* (1992) 357:80-82.
Banchereau et al., "Long-term human B cell lines dependent on interleukin-4 and antibody to CD40" *Science* (1991) 251:70-72.
Bordignon et al., "Retroviral vector-mediated high-efficiency expression of adenosine deaminase (ADA) in hematopoietic long-term cultures of ADA-deficient marrow cells" *Proc. Natl. Acad. Sci. USA* (1989) 86:6748-6752.
Caux et al., "Activation of human dendritic cells through CD40 cross-linking" *J. Exp. Med.* (1994) 180:1263-1272.
Cheng et al., "Involvement of CRAF1, a relative of TRAF, in CD40 signaling" *Science* (1995) 267:1494-1498.
Correll et al., "Production of human glucocerebrosidase in mice after retroviral gene transfer into multipotential hematopoietic progenitor cells" *Proc. Natl. Acad. Sci. USA* (1989) 868912-8916.

Culver, "Lymphocytes as cellular vehicles for gene therapy in mouse and man" *Proc. Natl. Acad. Sci. USA* (1991) 88:3155-3159.
Fuleihan et al., "Defective expression of the CD40 ligand in X chromosome-linked immunoglobulin deficiency with normal or elevated IgM" *Proc. Natl. Acad. Sci. USA* (1993) 90:2170-2173.
Harper et al., "The p21 Cdk-interacting protein Cip1 is a potent inhibitor of G1 cyclin-dependent kinases" *Cell* (1993) 75:805-816.
Herlyn et al., "Anti-idiotypic antibodies bear the internal image of human tumor antigen" *Science* (1986) 232:100-102.
Higuchi et al., "A general method of in vitro preparation and specific mutagenesis of DNA fragments: study of protein and DNA interactions" *Nucl. Acids Res.* (1988) 16:7351-7367.
Hu et al., "A novel RING finger protein interacts with the cytoplasmic domain of the CD40" *J. Biol. Chem.* (1994) 269:30069-30072.
Inui et al., "Identification of the intracytoplasmic region essential for signal transduction through a B cell activation molecule, CD40" *Eur. J. Immunol.* (1990) 20:1747-1753.
Korthäuer et al., "Defective expression of T-cell CD40 ligand causes X-linked immunodeficiency with hyper-IgM" *Nature* (1993) 361:539-541.
Liu et al., "Mechanism of antigen-driven selection in germinal centres" *Nature* (1989) 342:929-931.
Lupas et al., "Predicting coiled coils from protein sequences" *Science* (1991) 252:1162-1164.
Mosialos et al., "The Epstein-Barr virus transforming protein LMP1 engages signaling proteins for the tumor necrosis factor receptor family" *Cell* (1995) 80:389-399.
Ochs et al., "Advances in X-linked immunodeficiency diseases" *Curr. Opin. Pediatr.* (1993) 5:684-691.
Oi et al., "Chimeric antibodies" *BioTechniques* (1986) 4:214-221.
O'Rourke et al., "Thrombospondin 1 and thrombospondin 2 are expressed as both homo- and heterotrimers" *J. Biol. Chem.* (1992) 267:24921-24924.
Rill et al., "An approach for the analysis of relapse and marrow reconstitution after autologous marrow transplantation using retrovirus-mediated gene transfer" *Blood* (1992) 79:2694-2700.
Ron et al., "pGSTag—a versatile bacterial expression plasmid for enzymatic labeling of recombinant proteins" *BioTechniques* (1992) 13:866-869.
Sato et al., "A novel member of the TRAF family of putative signal transducing proteins binds to the cytosolic domain of CD40" *FEBS Letters* (1995) 358:113-118.
Spira et al., "The identification of monoclonal class switch variants by sib selection and an ELISA assay" *J. Immunol. Meth.* (1984) 74:307-315.
Stamenkovic et al., "A B-lymphocyte activation molecule related to the nerve growth factor receptor and induced by cytokines in carcinomas" *EMBO J.* (1989) 8:1403-1410.

(Continued)

*Primary Examiner*—Robert C Hayes
(74) *Attorney, Agent, or Firm*—Casimir Jones S.C.

(57) ABSTRACT

This invention provides a novel purified mammalian protein having the ability to bind the cytoplasmic region or domain of a CD40 receptor and the nucleic acid molecules coding for this protein. Also provided by this invention are antibodies which specifically bind CD40bp. Methods of using the proteins, nucleic acids and antibodies described above are further provided herein.

6 Claims, 8 Drawing Sheets

OTHER PUBLICATIONS

Staudinger et al., "Interactions among vertebrate helix-loop-helix proteins in yeast using the two-hybrid system" *J. Biol. Chem.* (1993) 268:4608-4611.

Studier, "Use of bacteriophage T7 lysozyme to improve an inducible T7 expression system" *J. Mol. Biol.* (1991) 219:37-44.

Torres et al., "Differential increase of an alternatively polyadenylated mRNA species of murine CD40 upon B lymphocyte activation" *J. Immunol.* (1992) 148:620-626.

Werner-Favre et al., "Similar CD40 ligand expression on EL-4 thymoma cell lines with widely different helper activity for B lymphocytes" *Immunol.* (1994) 81:111-114.

Yang et al., "A protein kinase substrate identified by the two-hybrid system" *Science* (1992) 257:680-682.

Zhang et al., "CD40 stimulation provides an IFN-τ-independent and IL-4-dependent differentiation signal directly to human B cells for IgE production" *J. Immunol.* (1991) 146:1836-1842.

Irie, S., et al., "A Novel cDNA Encoding a Protein that Binds the Cytoplasmic Domain of CD40," *J. Cell. Biochem.* (1995) Abstract Supplement 19A:36 (Abstract A1-234).

* cited by examiner

```
MESSKKMDSPGALQTNPPLKLHTDRSAGTPVFVPEQGGYKEKFVKTVEDKYKCEK    55
CHLVLCSPKQTECGHRFCESCMAALLSSSPKCTACQESIVKDKVFKDNCCKREI    110
LALQIYCRNESRGCAEQLMLGHLVHLKNDCHFEELPCVRPDCKEKVLRKDLRDHV   165
EKACKYREATCHCKSQVPMIALQKHEDTDCPCVVVSCPHKCSVQTLLRSELSAH    220
LSECVNAPSTCSFKRYGCVFQGTNQQIKAHEASSAVQHVNLLKEWSNSLERKVSL   275
LQNESVEKNKSIQSLHNQICSFEIEIERQKEMLRNNESKILHLQRVIDSQAEKLK   330
ELDKEIRPERQNWEEADSMKSSVESLQNRVTELESVDKSAGQVARNTGLLESQLS   385
RHDQMLSVHDIRLADMDLGFQVLETASYNGVLIWKIRDYKRRKQEAVMGKTLSLY   440
SQPFYTGYFGYKMCARVYLNGDGMGKGTHLSLFFVIMRGEYDALLPWPFKQKVTL   495
MLMDQGSSRRHLGDAFKPDPNSSSFKKPTGEMNIASGCPVFVAQTVLENGTYIKD   550
DTIFIKVIVDTSDLPDP                                         567
```

Figure 4A

| | | | |
|---|---|---|---|
| 49 | DKYKCEKCHLVLCSPKQT-EC--GHRFCESCMAALLSSSSPKCTACQ-ESIVK | 97 | CD40bp |
| 30 | AKYLCSACKNILRRPFQA-QC--GHRYCSFCLTSILSSGPQNCAACVYEGLYE | 79 | TRAF2 |
| 289 | KSISCQICEHILADPVET-NC--KHVFCRVCILRCLKVMGSYCPSCR-YPCFP | 337 | RAG1 |
| 15 | SELMCPICLDMLKNTMTTKEC--LHRFCSDCIVTALRSGNKECPTCR-KKLVS | 64 | RING1 |
| 12 | EEVTCPICLDPFVEPVSI-EC--GHSFCQECISQVGKGGGSVCPVCR-QRFLL | 60 | 52kd RNP |
| 30 | φAFRCHVCKDFYDSPMLT-SC--NHTFCSLCIRRCLSV-DSKCPLCR-ATDQE | 77 | UVS-2 |
| 23 | NKYTCPICFEFIYKKQIY-QCKSGHHACKECWEKSLET-KKECMTCK-SVVNS | 72 | DG17 |

```
389  QMLSVHDIRLADMDLGFQVLETASYNGVLINKIRDYKRRK   CD40bp
326  RSLGLKDLAMLQKVSELEVSTYDGVEIWKISDFTKRC     TRAF2
234  QTLAQKDQVLGKLEHSLRLMEASFDGTFLWKITNVTKRC   TRAF1

429  QEAVMGKTLSLYSQPFYIGYFGYKMCARVYLNGDGMGKGT  CD40bp
366  QEAVAGRTLPAIFSPAEYTSRYGYKMGLRVYLNGDGRGKT  TRAF2
274  HESVCGRTLPVSLFSPAFVTAKYIGYKLCLRLYLNGDSGKKT TRAF1

469  HLSLFFIMRGEYDALLPMPFKQKVTLHLMDQGSSRRHLG   CD40bp
406  HLSLFFVHMKGPNDALLQWPEINQKVTLMLDH-NNREHVI  TRAF2
314  HLSLFFIVHMRGEYDALLPMPEIRNKV.TFMLDQ-NNREHAI TRAF1

509  DAFKPDPNSSFKKPITGEMNHASGQPVFVAQTVEENG-IT  CD40bp
445  DAFRPDVLSSFQRPVSDMNIASGCPLECPVSKMEA-KNS   TRAF2
354  DAFRPDLSSASFQRPQSETNIVASGCPLFPLSKEQSPKHA  TRAF1

547  YIKDDTIFKVIVDTSDLPDP                      CD40bp
484  YVRDDAIFKAIVDLTGL                         TRAF2
394  YVKDDTMFLKCIVD-TSA                        TRAF1
```

Figure 5

```
ACGAAGGCCACGCGCCCGGCGCCCCTGAGCCGGCCGAGCGGCCGAGATGAGGAAAATGAGGCCCAAAGAAGTGATGC
CACTTGGTTAAGTCCTGACAGAGAGAAGAACTCCTCTTTCCTAGAATCAGAGATCAGAGAAACCTGCCTCTGCCTCCTGCTCCTACTCTTCTAAGG
ATCGCTGTCCTGACAGAGAGAGAACTCCTCTTTCCTAAAATGGAGTCGAGTAAAAGATGACTCTCCTGGCGCGCTCAGACTAAC
CCGCCGCTAAAGCTGCACACTGACCGCAGTGCTGGGACGCCAGTTTTTGTCCCTGAACAAGGAGGTTACAAGGAAAAGTTTGTGAA
GACCGTGGAGGACAAGTACAAGTGTGAGAAGTGCCACCTGGGTGCTGTGCAGCCGAAGCAGACCGAGTGTGGGCACCGCTTCTGCG
AGAGCTGCATGGCGCCCTGCTGAGCTCTTCAAGTCCAAAATGTACAGCGTGTCAAGAGAAGCATCGTTAAGATAAGGTGTTAAG
GATAATTGCTGCAAGAGAGAAATTCTGGCTCTTCAGATCTATTGTCGAATGAAAGCAGAGAGGTTGTGCAGAGCAGTTAATGCTGGG
ACATTCGGTGCATTTAAAAAATGATTGCCATTTTGAAGAACTTCCATGTGTCGTCTGCAAAGAAAAGTCTTGAGGAAAC
ACCTGCGAGACCACGTGGAAGGCGTGTAAATACCGGGAAGCCACATGCAGCCACTGTGTCCGAGAGTCAGGTTCCGAGATCGCTG
CAGAAACACGAAGACACCGACTGTCCCTGGTGGTGTCAATGCCCCAGCACACGTGTAGTTTTAAGCGCTATGCTCGTTTTCAGGGACAAACCAGC
GAGTGCACACTTGTCAGAGTGTGTCAAGCCCAGCTCCCGTCAGCAGCGACACCTGTAGTTTTAAGCGCTATGCTGAGGAGTGAACAACTCGCTGAAAGAAGGTTTCC
AGATCAAGGCCCACGAGGCCAGCTCCCGTCGACAAGAGCCATACAAGAGCATAGAGAGCATTGCACAATCAGATATGTAGCTTTGAAATTGAAG
TTGTTGCAGAATGAAGTGTAGAATAAATGCTTCGAAATAATGAATCCAAAATCTTCATTTACAGCGAGTGATAGACAGCCAAGCAGAGAAACTGAAGAGC
ACAAAAGGAAATGCTTCGAAATAATGCTTCGGCCAGAATCCGGCAGAACTGGGAGAAGTGCCAGGTCCTGGAGACCGCCAGTCAATGGAGTGCTCA
TTGACAAGGAGATCCGGCCCTTCCGGCAAGAGCGCGGGCAAGTGCCTGGAACAGAGCCGGCAAGTGCCTGTGAGTCCCAGCTGAGCCGGCATGACCA
ACCGAGCTGGAGAGCGTGGACAAGAGCGCGGGCTAGCGGGGAAGACACCCTGTCCTGCCTTTACAGCCAGCTTACGCCACTTGTCGCTGTTTTTGT
GATGCTGAGTGTGCACGACAATCCGCCTAGCGGGAAGGAGGAGCCCTCAGGGGACATGGAGAGCCCACTGTGTCCTGCCTTTACAGCCAGCTTACACT
TCTGGAAGATTCGGCGACTACAAGGTGTGCCAGGTCTACCTGAACGGGGACGGGGATGGGAAGAACTGTCATGTGATCAGGGGTCCTGCTGATCGGGGTCCTGTC
GGTTACTTTGGCTATGAAGATGATGCCCTGCTTCCTTGGCCGTTTAAGCAGAAGTGACACTCATGTGATGGATCAGGGGTCCTGTC
CATCATGCGTGAGAATATGATGCCCTGCTTCCTTGGCCGTTTAAGCAGAAGTGACACTCATGTGATGGATCAGGGGTCCTGTC
TTCACTGAGGTCCTGCGCTCAGAAAAGGACCTTGTGAGAGGAGGAAGCGGCAGAAGCGGCAGGCCCGGGAGGAGCCAC
GCGAGAGCACACTGACACGTTTTATATAATAGACTAGCCACACTTCACTCTGAAGAATTATTATCCTTCAACAAGATAAATATTGC
TGTCAGAAAGGTTTTCATTTTCATTTTTAAAGATCTAGTTAATTAAGGTGGAAAACATATGCTAAACAAAAGAAACATGATTT
TTCTTCCTTAAACTTGAACACCAAAACACACACACACGTGGGATAGCTGGACATGTCAGCATGTCGGACATGTGGGATAAGGA
GAATTTATGAAATAGTA
```

NUCLEIC ACIDS ENCODING CD40 BINDING PROTEIN

CROSS-REFERENCE TO RELATED APPLICATIONS

This application is a continuation of U.S. Ser. No. 08/826,577, filed Apr. 2, 1997, which in turn is a continuation of U.S. Ser. No. 08/404,832, filed Mar. 13, 1995, now abandoned, the contents of which are hereby incorporated by reference into the present disclosure.

This invention was made with government support under Grant No. CA61348, awarded by the National Institutes of Health. Accordingly, the United States government has certain rights in this invention.

FIELD OF THE INVENTION

This invention relates to a novel protein which binds to the intracellular region of the CD40 receptor.

BACKGROUND OF THE INVENTION

CD40 antigen is a cell surface transmembrane 45-kDa glycoprotein receptor expressed on a number of cell types, including B-lymphocytes ("B cells"). Stamenkovic et al. (1989) *EMBO J.* 8:1403-1410. It is a member of the tumor necrosis factor receptor family and, like other members, it appears to possess no intrinsic signaling capacity (e.g., kinase activity), suggesting that signal transduction is likely mediated by associating molecules. CD40 antigen has a short cytoplasmic tail (65 amino acid residues), and mutagenesis studies suggest that $Thr^{234}$ in the cytoplasmic domain is essential for signal transduction. Inui et al. (1990) *Eur. J. Immunol.* 20:1747-1753.

The ligand to CD40, "CD40L", is expressed on activated T-helper cells. Armitage et al. (1992) *Nature* 357:80-82. Activation of CD40 receptor is critical for B-cell proliferation, cytokine production, immunoglobulin class switching, and rescue of germinal center B cells from apoptosis following somatic mutation. Banchereau et al. (1991) *Science* 251:70-72; Liu et al. (1989) *Nature* 342:929-931; and Zhang et al. (1991) *J. Immunol.* 146:1836-1842.

Mutations in CD40L result in an immuno-deficiency (X-linked hyper-IgM syndrome) characterized by IgM-producing B cells that do not form germinal centers in response to foreign antigens. Allen et al. (1993) *Science* 259:990-993; Korthauer (1993) *Nature* 361:539-541; and Fuleihan (1993) *Proc. Natl. Acad. Sci. U.S.A.* 90:2170-2173. Hyper-IgM syndrome is a rare disorder characterized by recurrent infections and is associated with low serum levels of IgG, IgA, and IgE, and normal or increased levels of IgM. Clinical features of this syndrome include recurrent bacterial infections of the upper and lower respiratory tract, usually beginning in the first or second year of life. Ochs et al. (1993) *Curr. Opin. Pediatr.* 5:684-691. *Pneumocystis carinii* pneumonia in early infancy, neutropenia, thrombocytopenia, hemolytic anemia, nephritis and arthritis also have been associated with this genetic disorder.

Activation and transduction through the CD40 pathway is in large part, responsible for B cell activation and accordingly, the cellular immune response. However, it is still unknown how the receptor transduces its signal. Thus, in view of the variety of immune responses mediated through the CD40 receptor, it would be desirable to have a means to study the CD40 receptor pathway as well as modulate its effects. This invention satisfies this need and provides related advantages as well.

SUMMARY OF THE INVENTION

This invention provides a novel purified mammalian protein designated CD40bp having the ability to bind the cytoplasmic region or domain of a CD40 receptor.

Also provided by this invention are nucleic acid molecules that encode the mammalian protein which binds the intracellular domain of CD40.

An antibody, such as a monoclonal antibody, which specifically binds CD40bp is further provided by this invention.

Methods of using the proteins, nucleic acids and antibodies described above are further provided herein.

BRIEF DESCRIPTION OF THE FIGURES

In FIG. 3A, 293T cells were cotransfected with HA epitope-tagged CD40bp and with vector, mutant CD40 (CD40A), or native CD40 (CD40T) expression constructs, metabolically labeled with [$^{35}$S]methionine and [$^{35}$S]cysteine, and cell lysates analyzed by immunoprecipitation with an anti-CD40 monoclonal antibody. FIG. 3B shows that immune complexes from the native CD40T-transfected cells were dissociated and re-immunoprecipitated with control antibody (α-TSP), anti-CD40 (αCD40), or anti-HA tag (αHA), which should recognize HA-tagged CD40bp. FIG. 3C shows anti-CD40 immune complexes from transfected BJAB cells were either analyzed intact (α-CD40) or dissociated and reimmunoprecipitated with an anti-HA tag antibody (α-CD40/α-HA) or isotype-matched control antibody (α-CD40/Control Ig). Five-fold more cell lysate was used for the double immunoprecipitations. FIG. 3D is a northern blot analysis for CD40bp transcript expression in the SKW6.4 B-cell line. FIG. 3E is a survey of CD40bp transcript expression by RT-PCR. RNA from the indicated CD40-positive B-cell lines (B) and CD40-negative cell lines (T, T-cell line; E, epithelial cell line) was subjected to RT-PCR using CD40bp-specific oligonucleotide primers.

FIGS. 4A through 4E show the amino acid sequence and subsequent analysis of the CD40 binding protein. FIG. 4A is the amino acid sequence of CD40bp (also Seq. ID. No. 2). The first underlined segment is the RING finger domain; Cys/His residues that are invariant with respect to other proteins (shown in FIG. 4B) are indicated in bold. These amino acid sequences also are listed as: Seq. ID. No. 3 (CD40bp); Seq. ID. No. 4 (TRAF2); Seq. ID. No. 5 (RAG1); Seq. ID. No. 6 (RING1); Seq. ID. No. 7 (52 kd RNP); Seq. ID. No. 8 (UVS-2); and Seq. ID. No. 9 (DG17). The second underlined region represents the coiled-coil domain (shown in FIG. 4D). The Cys/His residues between the RING finger and coiled-coil domains are marked by asterisks. Features of the CD40bp sequence are summarized schematically in FIG. 4C. Homology within the C-terminal TRAF domains of the indicated proteins is shown in FIG. 4E (also Seq. ID Nos. 10 through 12).

FIG. 5 shows a nucleic acid sequence coding for full length CD40bp (also Seq. ID. No. 1). The initiation codon starts at nucleotide 211. The coding sequence ends at nucleotide 1911. The corresponding encoded amino acid sequence is shown in Seq. ID. No. 2.

DETAILED DESCRIPTION OF THE INVENTION

Proteins and Polypeptides

This invention provides purified proteins having the ability to bind the cytoplasmic region of the CD40 receptor. Previous attempts using traditional methods, including co-immunoprecipitation and chemical cross-linking, have failed to identify molecules associating with the cytoplasmic domain of the CD40 receptor. Thus, Applicants are the first to provide such molecules. The purified proteins of this invention, termed "CD40bp" are defined by their specific ability to bind to the cytoplasmic domain of the CD40 receptor. The CD40 receptor is present on various cell types, including for example, B cells, dendritic cells, epithelial cells, monocytes, blood mononuclear cells, and some carcinoma cell lines Any cell expressing CD40 is intended to be encompassed by the term "CD40+ cell". See Banchereau et al. (1991) *Science* 251:70-72; Caux et al. (1994) *J. Exp. Med.* 180:1263-1272; Fuleihan et al. (1993) *Proc. Natl. Acad. Sci.* 90:2170-2173; Werner-Favre et al. (1994) *Immunology* 81:111-114; and Stamenkovic et al. (1989) *Embo J.* 8:1403-1410.

In one embodiment of this invention, a purified protein is a human protein having an apparent molecular weight of about 64 kD as determined by an SDS polyacrylamide gel under reducing conditions. In a separate embodiment, a protein has the amino acid sequence shown in Seq. ID. No. 2 and FIG. 4A. Also provided by this invention are polypeptide fragments of the mammalian protein, the human 64 kD protein or the protein having the amino acid sequence shown in Seq. ID. No. 2 and FIG. 4E, each defined by the ability to bind to the cytoplasmic domain of the CD40 receptor using, for example, the in vitro binding assay described in Experiment II.

Figure 4C:

It is understood that functional equivalents of the protein shown in FIG. 4A, the 64 kD purified protein, or the polypeptide fragments thereof, e.g., as shown in FIG. 4B or 4EE, and equivalents thereof, also are within the scope of this invention. One such equivalent includes chemical structures other than amino acids which functionally mimic the binding of the CD40bp to the cytoplasmic domain of the CD40 receptor ("muteins"). An additional example of an equivalent is a protein or polypeptide containing a distinct protein or polypeptide joined to CD40bp or its equivalent which varies the primary sequence of protein of this invention from the sequences provided in FIG. 4A or 4E without necessarily affecting the binding of the resultant polypeptide or protein to the cytoplasmic domain of CD40. Where specific amino acids or other structures or sequences beyond the sequence shown in Seq. ID. No. 2 are presented, it is intended that various modifications which do not destroy the function of the binding site are within the definition of the proteins encompassed by this invention. For the purposes of this invention, the term "CD40bp" is intended to mean all of the proteins, polypeptides, fragments and equivalents thereof, having the ability to bind the cytoplasmic domain of CD40.

An agent having the ability to inhibit the ability of CD40bp to bind to the cytoplasmic domain of CD40 receptor is further provided by this invention. Such agents include, but are not limited to, an anti-CD40 bp antibody, a dominant inhibitory fragment of CD40bp or a soluble intracellular CD40. "Soluble intracellular CD40" is an intracellular portion of the CD40 receptor which binds CD40bp. These soluble receptors can be produced using the sequence of the cytoplasmic domain provided in Stamenkovic et al. (1989) supra and methods well known to those of skill in the art.

The terms "proteins" and "polypeptides" also are intended to include molecules containing amino acids linearly coupled through peptide bonds. As used herein, the term "peptide bond" or "peptide linkage" refers to an amide linkage between a carboxyl group of one amino acid and the α-amino group of another amino acid. Such polypeptides also can contain amino acid derivatives or non-amino acid moieties. The amino acids can be in the L or D form so long as the binding function of the polypeptide is maintained. The term amino acid refers both to the naturally occurring amino acids and their derivatives, such as TyrMe and PheCl, as well as other moieties characterized by the presence of both an available carboxyl group and an amine group. Non-amino acid moieties which can be contained in such polypeptides include, for example, amino acid mimicking structures. Mimicking structures are those structures which exhibit substantially the same spatial arrangement of functional groups as amino acids but do not necessarily have both the α-amino and α-carboxyl groups characteristic of amino acids.

As used herein, the term "hydrophobic" is intended to include those amino acids, amino acid derivatives, amino acid mimics and chemical moieties which are non-polar. Hydrophobic amino acids include Phe, Val, Trp, Ile and Leu. As used herein, the term "positively charged amino acid" refers to those amino acids, amino acid derivatives, amino acid mimics and chemical moieties which are positively charged. Positively charged amino acids include, for example, Lys, Arg and His.

The proteins and polypeptides of this invention are distinct from native or naturally occurring proteins or polypeptides because they exist in a purified state. As used herein, the term "purified" when referring to a protein or a polypeptide or any of the intended variations as described herein shall mean that the compound or molecule is substantially free of contaminants normally associated with a native or natural environment.

The proteins and polypeptides of this invention can be obtained by a number of methods well known to those of skill in the art, which include purification, chemical synthesis and recombinant methods. For example, the proteins and polypeptides can be purified from $CD40^+$ cell or tissue lysates using methods such as immuno-precipitation with anti-CD40bp antibody, and standard techniques such as gel filtration, ion-exchange, reversed-phase, and affinity chromatography using a CD40 fusion protein as shown herein. For such methodology, see for example Deutscher et al., *Guide to Protein Purification: Methods in Enzymology* (1990) Vol. 182, Academic Press.

The proteins and polypeptides also can be obtained by chemical synthesis using a commercially available automated peptide synthesizer such as those manufactured by Applied Biosystems, Inc., Model 430A or 431A, Foster City, Calif. and the amino acid sequence provided in FIG. 4A. The material so synthesized can be precipitated and further purified, for example by high performance liquid chromatography (HPLC).

Alternatively, the proteins and polypeptides can be obtained by well-known recombinant methods as described, for example, in Sambrook et al., *Molecular Cloning: A Labo-* ratory Manual 2d ed. (Cold Spring Harbor Laboratory (1989)) using the host vector systems described and exemplified below. As an example, CD40bp fusion protein can be made by first utilizing a CD40⁻ cell line such as 293T cells. The cells are first transiently transfected with pHATagCD40bp (constructed as described below). About 72 to 96 hours after transfection, the cells are lysed in 50 mMTris Ph7.6+1% NP-40. CD40bp fusion protein is purified from the cell-extract using standard immunochemical means since it contains an hemagglutinin epitope tag allowing one to use commercially available anti-HA monoclonal antibody to purify the tagged molecule.

The CD40b protein and polypeptides have several utilities. For example, they can be bound to a column and used for the purification of CD40 receptors or to detect CD40 in a cell or tissue sample. They also are useful as immunogens for the production of anti-CD40bp antibodies as described below. They have further utility in an in vitro assay system to screen for immunosuppressant drugs and to test possible therapies.

When used to detect CD40, the CD40bp can be bound to a solid phase carrier for example, glass, polystyrene, polyethylene, dextran, nylon, natural and modified celluloses, polyacrylamides, glutathione-agarose beads and agaroses. Those skilled in the art will know of other suitable carriers for this purpose. Accordingly, this invention also provides a method of detecting CD40 in a cell sample by first immobilizing CD40bp onto a solid support such as glutathione-agarose beads at a suitable concentration, eg., between about 5 mg/ml to about 12 mg/ml, and more preferably between about 6 mg/ml and about 10 mg/ml. The sample containing or suspected of containing CD40 is prepared and contacted with the beads under conditions favoring binding between the CD40 receptor and CD40bp. Suitable conditions are for example, those set forth in Experiment II. The beads are then subjected to conditions to release the complex from the solid support and protein complex can then be visualized by autoradiography.

The proteins of this invention also can be combined with various liquid phase carriers, such as sterile or aqueous solutions, pharmaceutically acceptable carriers as defined below, suspensions and emulsions. Examples of non-aqueous solvents include propyl ethylene glycol, polyethylene glycol and vegetable oils. When used to prepare antibodies, the carriers also can include an adjuvant which is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides.

Nucleic Acids

Isolated nucleic acid molecules which encode amino acid sequences corresponding to CD40bp protein, mutein, antibodies and active fragments thereof are further provided by this invention. As used herein, "nucleic acid" shall mean single and double stranded DNA, cDNA and RNA, including anti-sense RNA. One can obtain an anti-sense RNA using the sequence provided in FIG. 5 and the methodology described in Vander Krol et al. (1988) *BioTechniques* 6:958. "Isolated" means separated from other cellular components normally associated with DNA or RNA intracellularly.

In one aspect of this invention, the nucleic acid molecule encoding CD40bp protein or polypeptide has the sequence or parts thereof shown in FIG. 5.

The invention also encompasses nucleic acid molecules which differ from that of the nucleic acid molecules shown in FIG. 5, but which produce the same phenotypic effect. These altered, but phenotypically equivalent nucleic acid molecules are referred to "equivalent nucleic acids." Examples of such "equivalent nucleic acids" are those molecules which have a sequence which is homologous to sequence of FIG. 5 and preferably have a homology of greater than about 50%, more preferably in excess of 90%. A homology of about 99% is most preferred. This invention also encompasses nucleic acid molecules characterized by changes in non-coding regions that do not alter the phenotype of the polypeptide produced therefrom when compared to the nucleic acid molecule described hereinabove. This invention further encompasses nucleic acid molecules which hybridize to the nucleic acid molecule of the subject invention.

The nucleic acid molecules of this invention can be isolated using the technique described in Experiment I or replicated using PCR (Perkin-Elmer) and the methods described in Experiment III. For example, the sequence can be chemically replicated using PCR (Perkin-Elmer) which in combination with the synthesis of oligonucleotides, allows easy reproduction of DNA sequences. A DNA segment of up to approximately 6000 base pairs in length can be amplified exponentially starting from as little as a single gene copy by means of PCR. In this technique, a denatured DNA sample is incubated with two oligonucleotide primers that direct the DNA polymerase-dependent synthesis of new complementary strands. Multiple cycles of synthesis each afford an approximate doubling of the amount of target sequence. Each cycle is controlled by varying the temperature to permit denaturation of the DNA strands, annealing the primers, and synthesizing new DNA strands. The use of a thermostable DNA polymerase eliminates the necessity of adding new enzyme for each cycle, thus permitting fully automated DNA amplification. Twenty-five amplification cycles increase the amount of target sequence by approximately $10^6$-fold. The PCR technology is the subject matter of U.S. Pat. Nos. 4,683,195, 4,800,159, 4,754,065, and 4,683,202. Alternatively, one of skill in the art can use the sequence provided herein and a commercial DNA synthesizer to replicate the DNA. RNA can be obtained by using the isolated DNA and inserting it into a suitable cell where it is transcribed into RNA. The RNA can then be isolated using methods well known to those of skill in the art, for example, as set forth in Sambrook et al. (1989) supra.

The invention further provides the isolated nucleic acid molecule operatively linked to a promoter of RNA transcription, as well as other regulatory sequences for replication and/or expression of the DNA or RNA. As used herein, the term "operatively linked" means positioned in such a manner that the promoter will direct the transcription of RNA off the nucleic acid molecule. Examples of such promoters are SP6, T4 and T7. Vectors which contain a promoter or a promoter/enhancer, with termination codons and selectable marker sequences, as well as a cloning site into which an inserted piece of DNA can be operatively linked to that promoter are well known in the art. See for example, Gacesa and Ramji, *Vectors: Essential Data Series* (1994) John Wiley & Sons, N.Y., which contains maps, functional properties, commercial suppliers and a reference to GenEMBL accession numbers for various suitable vectors. Preferable, these vectors are capable of transcribing RNA in vitro or in vivo.

Fragments of the sequence shown in FIG. 5 and its equivalents are useful as probes to identify transcripts of the protein which may or may not be present. These nucleic acid fragments can by prepared, for example, by restriction enzyme digestion of the nucleic acid molecule of FIG. 5 and then labeled with a detectable marker such as a radioisotope using well known methods. Alternatively, random fragments can be generated using nick translation of the molecule. For methodology for the preparation and labeling of such fragments, see Sambrook et al., *Molecular Cloning: A Laboratory Manual* Cold Spring Harbor Press, Cold Spring Harbor, N.Y. (1989) supra. Nucleic acid fragments of at least 10 nucleotides are useful as hybridization probes. Isolated nucleic acid fragments also are useful to generate novel peptides. These peptides, in turn, are useful as immunogens for the generation of polyclonal and monoclonal antibodies.

As noted above, an isolated nucleic acid molecule of this invention can be operatively linked to a promoter of RNA transcription. These nucleic acid molecules are useful for the recombinant production of CD40bp proteins and polypeptides or as vectors for use in gene therapy. Accordingly, this invention also provides a vector having inserted therein an isolated nucleic acid molecule described above, for example, a viral vector, such as bacteriophages, baculoviruses and retroviruses, or cosmids, plasmids and other recombination vectors. Nucleic acid molecules are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers can be ligated to the insert DNA that correspond to a restriction site in the vector DNA, which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human cytomegalovirus (CMV) for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA.

An additional example of a vector construct of this invention is a bacterial expression vector including a promoter such as the lac promoter and for transcription initiation, the Shine-Dalgarno sequence and the start codon AUG (Sambrook et al., (1989) supra). Similarly, a eucaryotic expression vector is a heterologous or homologous promoter for RNA polymerase II, a downstream polyadenylation signal, the start codon AUG, and a termination codon for detachment of the ribosome. Such vectors can be obtained commercially or assembled by the sequences described in methods noted above.

Expression vectors containing these nucleic acids are useful to obtain host vector systems to produce CD40bp proteins and polypeptides. It is implied that these expression vectors must be replicable in the host organisms either as episomes or as an integral part of the chromosomal DNA. Suitable expression vectors include viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a procaryotic or a eucaryotic cell and the host cell replicates, CD40bp can be recombinantly produced. Suitable host cells will depend on the vector and can include mammalian cells, animal cells, human cells, simian cells, insect cells, yeast cells, and bacterial cells constructed using well known methods. See Sambrook et al., (1989) supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; or DEAE-dextran; electroporation; or microinjection. See Sambrook et al. (1989) supra for this methodology. Thus, this invention also provides a host cell, e.g. a mammalian cell, a animal cell, a human cell, or a bacterial cell, containing a nucleic acid molecule encoding a CD40bp protein or polypeptide.

Using the host vector system described above, a method of producing recombinant CD40bp or active fragments thereof is provided by growing the host cells described herein under suitable conditions such that the nucleic acid encoding the CD40 protein or polypeptide is expressed. Suitable conditions can be determined using methods well known to those of skill in the art, see for example, Sambrook et al., (1989) supra. Proteins and polypeptides purified from the cellular extract and thereby produced in this manner also are provided by this invention.

A vector containing the isolated nucleic acid encoding CD40bp also is useful for gene therapy to modulate $CD40^+$ cellular functions such as CD40-regulated antibody production and immune disorders caused by CD40 disfunction. The terms "$CD40^+$ cellular function" is intended to mean cellular functions which are affected by the binding of the receptor to its ligands, i.e., CD40L and CD40bp, alone or in combination with each other. In some instances, it is desirable to augment $CD40^+$ function to increase production of antibodies by introducing into the cell CD40bp protein or nucleic acid. A related CD40 immune disfunction wherein CD40 function is suitably augmented is Hyper-IgM Syndrome. In other instances, it is desirable to down-regulate $CD40^+$ cellular function by introducing into the cell a CD40bp antibody or a nucleic acid encoding an anti-CD40bp antibody or alternatively, a CD40bp fragment or nucleic acid encoding it which is a dominant negative inhibitor of functionally intact native CD40bp. This therapy will inhibit or disable CD40 signaling and therefore is a useful therapy where constitutive, unabated activation of B cells leads to production of inordinate amounts of antibodies contributing to an autoimmune disease or state.

When used for gene therapy, a pharmaceutically acceptable vector is preferred, such as a replication-incompetent retroviral vector. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller, A. D. et al., (1989) *BioTechniques* 7:980-990). The methodology of using replication-incompetent retroviruses for retroviral-mediated gene transfer of gene markers is well established (Correll, et al. (1989), *PNAS USA* 86:8912; Bordignon, (1989), *PNAS USA* 86:8912-52; Culver, K., (1991), *PNAS USA* 88:3155; and Rill, D. R. (1991), *Blood* 79(10):2694-700. Clinical investigations have shown that there are few or no adverse effects associated with the viral vectors, see Anderson, (1992), *Science* 256:808-13.

Antibodies

Also provided by this invention is an antibody capable of specifically forming a complex with CD40bp protein or a fragment thereof, as well as nucleic acids encoding them.

Vectors and host cells containing these nucleic acids also are encompassed by this invention. The term "antibody" includes polyclonal antibodies and monoclonal antibodies. The antibodies include, but are not limited to mouse, rat, rabbit or human antibodies.

As used herein, an "antibody or polyclonal antibody" means a protein that is produced in response to immunization with an antigen or receptor. The term "monoclonal antibody" means an immunoglobulin derived from a single clone of cells. All monoclonal antibodies derived from the clone are chemically and structurally identical, and specific for a single antigenic determinant. The hybridoma cell lines producing the monoclonal antibodies also are within the scope of this invention.

Laboratory methods for producing polyclonal antibodies and monoclonal antibodies, as well as deducing their corresponding nucleic acid sequences, are known in the art, see Harlow and Lane, *Antibodies: A Laboratory Manual*, Cold Spring Harbor Laboratory, New York (1988) and Sambrook et al. (1989) supra. The monoclonal antibodies of this invention can be biologically produced by introducing CD40bp or a fragment thereof into an animal, e.g., a mouse or a rabbit. The antibody producing cells in the animal are isolated and fused with myeloma cells or heteromyeloma cells to produce hybrid cells or hybridomas. Accordingly, the hybridoma cells producing the monoclonal antibodies of this invention also are provided.

Thus, using the CD40bp protein or fragment thereof, and well known methods, one of skill in the art can produce and screen the hybridoma cells and antibodies of this invention for antibodies having the ability to bind CD40bp.

If a monoclonal antibody being tested binds with CD40bp, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding CD40bp with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with CD40bp with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of a different isotype than the monoclonal antibody of this invention. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) *Proc. Natl. Acad. Sci.* 82:8653 or Spira et al. (1984) *J. Immunol. Methods* 74:307. Thus, the monoclonal antibodies of this invention would include class-switch variants having specificity for an epitope on CD40bp.

This invention also provides biological active fragments of the polyclonal and monoclonal antibodies described above. These "antibody fragments" retain some ability to selectively bind with its antigen or immunogen. Such antibody fragments can include, but are not limited to:

(1) Fab, the fragment which contains a monovalent antigen-binding fragment of an antibody molecule produced by digestion with the enzyme papain to yield an intact light chain and a portion of one heavy chain;

(2) Fab', the fragment of an antibody molecule obtained by treating with pepsin, followed by reduction, to yield an intact light chain and a portion of the heavy chain; two Fab' fragments are obtained per antibody molecule;

(3) (Fab')$_2$, the fragment of the antibody that is obtained by treating with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) SCA, defined as a genetically engineered molecule containing the variable region of the light chain, the variable region of the heavy chain, linked by a suitable polypeptide linker as a genetically fused single chain molecule.

A specific examples of "biologically active antibody fragment" include the CDR regions of the antibodies. Methods of making these fragments are known in the art, see for example, Harlow and Lane, (1988) supra.

The antibodies of this invention also can be modified to create chimeric antibodies (Oi, et al. (1986) *BioTechniques* 4(3):214). Chimeric antibodies are those in which the various domains of the antibodies' heavy and light chains are coded for by DNA from more than one species.

The isolation of other hybridomas secreting monoclonal antibodies with the specificity of the monoclonal antibodies of the invention can also be accomplished by one of ordinary skill in the art by producing anti-idiotypic antibodies (Herlyn, et al., *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in this instance, the anti-idiotypic monoclonal antibody could be used for immunization for production of these antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics. Also encompassed by this invention are proteins or polypeptides that have been recombinantly produced, biochemically synthesized, chemically synthesized or chemically modified, that retain the ability to bind CD40bp or a fragment thereof, as the corresponding native polyclonal or monoclonal antibody.

The antibodies of this invention can be linked to a detectable agent or a hapten. The complex is useful to detect the CD40bp protein and fragments in a sample using standard immunochemical techniques such as immunohistochemistry as described by Harlow and Lane (1988) supra. Examples of types of immunoassays which can utilize monoclonal antibodies of the invention are competitive and non-competitive immunoassays in either a direct or indirect format. Examples of such immunoassays are the enzyme linked immunoassay (ELISA) radioimmunoassay (RIA) and the sandwich (immunometric) assay. Detection of CD40bp using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitropherryl, pyridoxal, and fluorescein, which can react with specific anti-hapten antibodies. See Harlow and Lane (1988) supra.

The monoclonal antibodies of the invention can be bound to many different carriers. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, CD40bp may be detected by the monoclonal antibodies of the invention when present in biological fluids and tissues. Any sample of $CD40^+$ cell or tissue lysate containing a detectable amount of CD40bp can be used.

Compositions

This invention also provides compositions containing any of the above-mentioned proteins, muteins, polypeptides or fragments thereof, and an acceptable solid or liquid carrier. When the compositions are used pharmaceutically, they are combined with a "pharmaceutically acceptable carrier" for administration. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, *Remington's Pharm. Sci.*, 15th Ed (Mack Publ. Co., Easton (1975)). These compositions can be used for the preparation of medicaments for the diagnosis and treatment of pathologies associated with the loss of functional CD40bp.

Utilities

The antibodies and nucleic acid molecules of this invention also are useful to detect and determine the presence of CD40bp in a cell or a sample taken from a patient. Because the presence of CD40bp in a cell is an important indicator of immune function and CD40 disfunction; the absence of CD40bp has been implicated in a number of immunological diseases, such as systemic lupus. It is therefore advantageous to use the antibody to screen for the presence or absence of CD40bp in a $CD40^+$ or $CD40^+$ tissue sample cell extract taken from a subject. This procedure is preferred over the use of hybridization assays to detect CD40bp transcript levels because it is a precise indicator of loss of CD40bp in the cells. That is, CD40bp transcript may be present in the cell but not translated thereby leading to the CD40bp deficiency and immune disfunction.

CD40bp also is useful to detect the presence of CD40 in a cell or tissue sample suspected of containing the receptor. The sample is prepared using methods well known in the art (see, for example, Armitage et al. (1992) *Nature* 357:80-82; Armitage et al. (1993) *Eur. J. Immunol.* 23:2326-2331; Caux et al. (1994) *J. Exp. Med.* 180:1263-1272; Torres and Clark (1992) *J. of Immunol.* 148(2):620-626; and Werner-Favre, et al. (1994) 81:111-114). A CD40bp or polypeptide is then added to the sample under conditions favoring binding of the protein to the receptor for example, as provided in Example II.

The use of the compositions and methods in vitro provides a powerful bioassay for screening for drugs which are agonists or antagonists of CD40 pathway function in these cells. It also provides a powerful assay to determine whether an agent of interest, such as a pharmaceutical, is useful to treat a CD40 related disorder or to further augment CD40 function. For example, the composition to be tested can be added prior to, simultaneously or subsequent to CD40bp as described above. A separate "control", assay is run simultaneously under the same conditions but without the addition of the composition or drug being tested. If the agent inhibits binding of CD40 to CD40bp (as compared to control) the agent is a candidate for immunosuppressive therapy. If the agent augments binding, then the agent is a candidate for immunotherapy for conditions such as hyper-IgM syndrome.

Accordingly, this invention also provides a method for screening for a CD40 immunosuppressive agent, comprising the steps of: a) providing a CD40 cytoplasmic domain receptor bound to a solid support; b) contacting the agent with the receptor bound support of step a) under conditions favoring binding of the cytoplasmic domain to the receptor to CD40bp; c) contacting detectably-labeled CD40bp to the solid support of step b) under conditions favoring binding of CD40 cytoplasmic domain receptor to CD40bp; d) detecting the presence of any complex formed between CD40 receptor and CD40bp to form CD40 receptor-CD40bp complex; and e) the absence of CD40 receptor-CD40bp complex being indicative that the agent inhibits binding of CD40bp to CD40 receptor and therefore is an immunosuppressive agent.

This invention provides an alternative method for screening for a CD40 immunosuppressive agent, which comprises the steps of a) providing a CD40 cytoplasmic domain receptor bound to a solid support; b) contacting detectably-labeled CD40bp to the solid support of step a) under conditions favoring binding of CD40 cytoplasmic domain receptor to —CD40bp; c) contacting the agent to be screened with the receptor bound support of step b) under conditions favoring binding of the cytoplasmic domain to the receptor to CD40bp; d) detecting the presence of any complex formed between CD40 receptor and CD40bp to form CD40 receptor-CD40bp complex; and e) the absence of CD40 receptor-CD40bp complex being indicative that the agent inhibits binding of CD40bp to CD40 receptor and therefore is an immunosuppressive agent.

As is apparent to those of skill in the art, the above compositions can be combined with instructions for use to provide a kit for a commercially available screen.

The compositions provided herein also are useful to modulate the CD40 receptor pathway and cellular functions associated with this pathway, for example, CD40-related cytokine production, B cell proliferation, and hyper-IgM syndrome. Additional CD40-related functions are known to those of skill in the art. (See, for example, those disclosed in PCT Publications WO 93/08207 and WO 94/04570 and European Patent Publication Nos. 555 880 A2 and 585 943 A2).

When a function associated with the CD40 pathway should be augmented, nucleic acid molecules coding for CD40bp can be inserted into a $CD40^+$ cell, such as a B cell, using an appropriate pharmaceutical vector. Alternatively, when a function, associated with the CD40 pathway should be suppressed a nucleic acid coding for CD40bp fragment, a dominant inhibitory CD40bp polypeptide fragment, or anti-sense CD40bp RNA can be introduced into a $CD40^+$ cell using an appropriate pharmaceutical vector.

This method can be practiced in vitro, ex vivo or in vivo. When the method is practiced in vitro or ex vivo, the expression vector, protein or polypeptide can be added to the cells in culture or taken from a subject or added to a pharmaceutically acceptable carrier as defined below. In addition, the expression vector or CD40bp DNA can be inserted into the target cell using well known techniques such as transfection, electroporation or microinjection.

More specifically, the in vitro assay method comprises culturing suitable cell cultures or tissue cultures under conditions (temperature, growth or culture medium and gas ($CO_2$)) and for an appropriate amount of time to attain exponential proliferation without density dependent constraints. Suitable cell or tissue cultures or $CD40^+$ or $CD40^-$. In one embodiment, the cells are then exposed to preliminary conditions for CD40 activation, e.g., by exposing them to CD40L or to CD40 antibodies such as those described in Armitage et al. (1992) supra, Armitage et al. (1993) supra, Caux et al. (1994) supra, Torres and Clark (1992) supra, or Werner-Favre et al. (1994) supra. CD40L and CD40 antibodies are well known to those of skill in the art. (See PCT Publication Nos. WO 93/08207 supra and 94/04570) supra. The "activated" cells are again cultured under suitable temperature and time conditions. In some embodiments, a drug or agent to be tested is added in varying concentrations at a time that is simultaneous with, prior to, or after the activating agent.

The nucleic acid or protein of this invention is then added to the culture in an effective amount and the cells are cultured under suitable temperature and time conditions to effect transcription of the nucleic acid or binding of the protein to the receptor. The nucleic acid or protein can be added prior to, simultaneously with, or after, the activating agent. The cells are assayed for CD40 activity using methods well known to those of skill in the art and described herein, for example, by monitoring CD40-associated IgG production. It is apparent to those of skill in the art that two separate culture of cells must be treated and maintained as the test population. One is maintained without receiving an activating agent to determine background release and the second without receiving the agent to be tested. This second population of cells acts as a control.

When the method is practiced in vivo in a human patient or when activated cells are treated ex vivo, it is unnecessary to provide the activating agent since it is provided by the patient's immune system. However, when practiced in an experimental animal model, it can be necessary to provide an effective amount of the activating agent in a pharmaceutically acceptable carrier prior to administration of the nucleic acid or protein to activate $CD40^+$ cells. When the method is practiced in vivo, the carrying vector, polypeptide, polypeptide equivalent, or expression vector can be added to a pharmaceutically acceptable carrier and systemically administered to the subject, such as a human patient or an animal such as a mouse, a guinea pig, a simian, a rabbit or a rat. Alternatively, it can be directly infused into the cell by microinjection.

When practiced in vivo, the compositions and methods are particularly useful for maintaining CD40 function in a subject or an individual suffering from or predisposed to suffer from CD40-related disfunction, such as Hyper-IgM Syndrome. When the animal is an experimental animal such as a mouse, this method provides a powerful assay to screen for new drugs that may be used alone or in combination with this invention to ameliorate or reduce the symptoms and infections associated with CD40-related disfunction.

As used herein, the term "administering" for in vivo purposes means providing the subject with an effective amount of the nucleic acid molecule, polypeptide or antibody, effective to modulate CD40-related function of the target cell. Methods of administering pharmaceutical compositions are well known to those of skill in the art and include, but are not limited to, microinjection, intravenous or parenteral administration. The compositions are intended for topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the vector used for therapy, the polypeptide or protein used for therapy, the purpose of the therapy, the target cell being treated, and the subject being treated. Single or multiple administrations can be carried out with the dose level and pattern being selected by the treating physician.

The compositions also can be administered to subjects or individuals susceptible to or at risk of developing a CD40-related disease. In one embodiment, the composition can be administered to a subject susceptible to CD40-related lymphocyte disfunction to maintain-lymphocyte cell function such as antibody production. In these instances, a "prophylactically effective amount" of the composition is administered which is defined herein to be an amount that is effective to maintain the targeted CD40 function, such as lymphocyte function, at an acceptable level.

It should be understood that by preventing or inhibiting CD40 disfunction in a subject or individual, the compositions and methods of this invention also provide methods for treating, preventing or ameliorating the symptoms associated with a disease characterized by CD40 disfunction.

The following examples are provided merely to illustrate, but not limit, the invention described herein.

EXPERIMENT I

Yeast Two-hybrid Screen—Using a modification of the method of Harper et al. (1993) *Cell* 75:805-816, a hybrid gene encoding the GAL4 DNA-binding domain (amino acids 1-147), hemagglutinin ("HA") epitope tag, and CD40 cytoplasmic region (amino acids 216-279) was constructed in the yeast bait vector pAS1CYH2. This construct was designated GAL4CD40, and expression of the fusion protein was confirmed by anti-HA immunoblotting. This bait plasmid was cotransformed with a human B-cell cDNA expression library (prey) fused to the activation domain of GAL4 in the pACT plasmid. Interaction between bait- and prey-encoded genes in the Y190 yeast strain reconstitutes GAL4 as an active transcriptional complex, allowing growth in the absence of histidine and activation of the β-galactosidase reporter gene. Thirty-six of the $10^6$ transformants screened grew in the absence of histidine and had detectable β-galactosidase staining within 10 minutes of incubation with the chromogenic substrate 5-bromo-4-chloro-3-indolyl β-D-galactoside. Plasmids recovered from the original yeast strains were used in a cotransformation assay with GAL4CD40 or control heterologous baits. Twelve plasmids encoded proteins that interacted with native CD40 but not with the control heterologous baits. DNA sequencing revealed 9 of 12 to encode the same protein, designated CD40-binding protein (CD40bp). Cotransformation assays were repeated in the yeast Y190 strain, where CD40bp fused to the activation domain of GAL4 was cotransformed with native CD40 (pCD40T) or the indicated heterologous baits expressed as fusions with the DNA-binding domain of GAL4. These included mutant CD40 (where $Thr^{234}$ was changed to an alanine: pCD40A), the cytoplasmic domain of the p55 TNF receptor (pTNFR amino acids 206-426), FAS receptor cytoplasmic domain (pFAS amino acids 178-319), truncated p55 TNF receptor cytoplasmic domain missing 20 C-terminal residues (ΔTNFR amino acids 206-406), the helix-loop-helix motif of E12 (amino acids 508-564) (from Staudinger et al. (1993) *J. Biol. Chem.* 268:4608-4611) and the yeast Ser-Thr kinase SNF1 (from Yang et al. (1992) *Science* 257:680-682). Colonies from each transformation were patched onto a selective plate and a β-galactosidase assay performed on yeast transferred to nitrocellulose filters and permeabilized in liquid nitrogen as described in Harper et al. (1993) supra.

Figure 1:
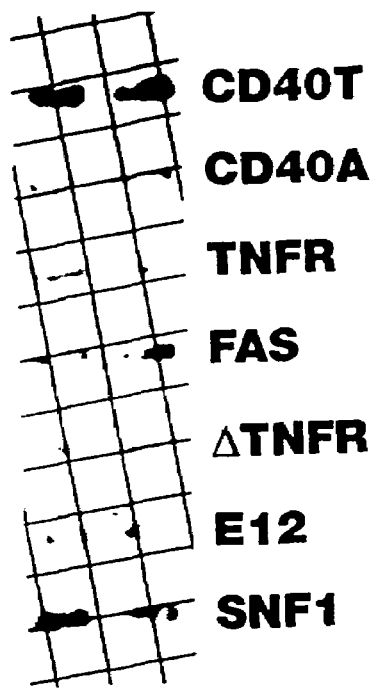
FIG. 1 shows CD40bp interactions with hybrid proteins. Yeast transformants harboring CD40bp fused to the activation domain of GAL4 and the indicated expression plasmids encoding proteins fused to the DNA-binding domain of GAL4 were assayed in duplicate for β-galactosidase activity.

Nine independent clones were found to encode the same protein, designated CD40-binding protein (CD40bp) in the yeast Y190 strain (FIG. 1). To assess whether the interaction of CD40bp was specific to native CD40, a mutant CD40 bait was created in which $Thr^{234}$ was converted to Ala (pCD40A), an alteration known to disable CD40 signaling. In addition, other heterologous baits, including the cytoplasmic domains of the related TNF and FAS receptors, were tested in a cotransformation assay. As shown in FIG. 1, CD40bp interacted with native CD40 only but not with mutant CD40 or the other heterologous baits, showing that the CD40-CD40bp interaction was specific as measured by the yeast cotransformation assay.

EXPERIMENT II

GST Fusion Protein Expression and In Vitro Binding Assay—Native (CD40T) and mutant (CD40A) CD40 sequences used in the construction of the yeast bait vectors were excised and subcloned into the glutathione S-transferase ("GST") fusion protein vector pGSTag (as described in Ron et al. (1992) *BioTechniques* 13:866-869) and transformed into the *Escherichia coli* strain BL21 (DF3) pLysS (as described in Studier et al. (1991) *J. Mol. Bio.* 219:37-44). GST and GST fusion proteins were prepared using published procedures of Studier et al. (1991) supra, and the recombinant proteins were immobilized onto glutathione-agarose beads at a concentration of about 8 mg/ml (as described in Harper et al. (1993) supra).

Labeled CD40bp was prepared by in vitro transcription translation using the TNT T7-coupled reticulocyte lysate system from Promega according to the manufacturer's instructions. Briefly, a 2.2-kilobase pair cDNA encoding CD40bp was excised from the yeast prey vector (pACT) using XhoI and subcloned into the pBluescript II plasmid (Stratagene), which had a flanking T7 promoter allowing generation of sense strand transcript. The luciferase construct was provided by the vendor and could similarly be transcribed by T7 polymerase.

Following translation, 5 μl of total $^{36}S$ labeled reticulocyte lysate was either subjected to SDS-polyacrylamide gel electrophoresis and fluorography or diluted into 1 ml of GST binding buffer (10 mM Tris, pH 7.6, 50 mM NaCl, 5 mM EDTA, 1% Triton X-100, 0.1% bovine serum albumin, 1 mM phenylmethylsulfonyl fluoride), and incubated with 40 μl of a 50% slurry of GST-, GSTCD40T-, or GSTCD40A-agarose beads for 2 hours at 4° C., following which the beads were pelleted by pulse centrifugation in a micrdcentrifuge, washed three times in GST buffer (without bovine serum albumin), boiled in SDS-sample buffer, and resolved on a 10% SDS-acrylamide gel. Bound proteins were visualized following autoradiography at −80° C. for 1 hour.

Figure 2:
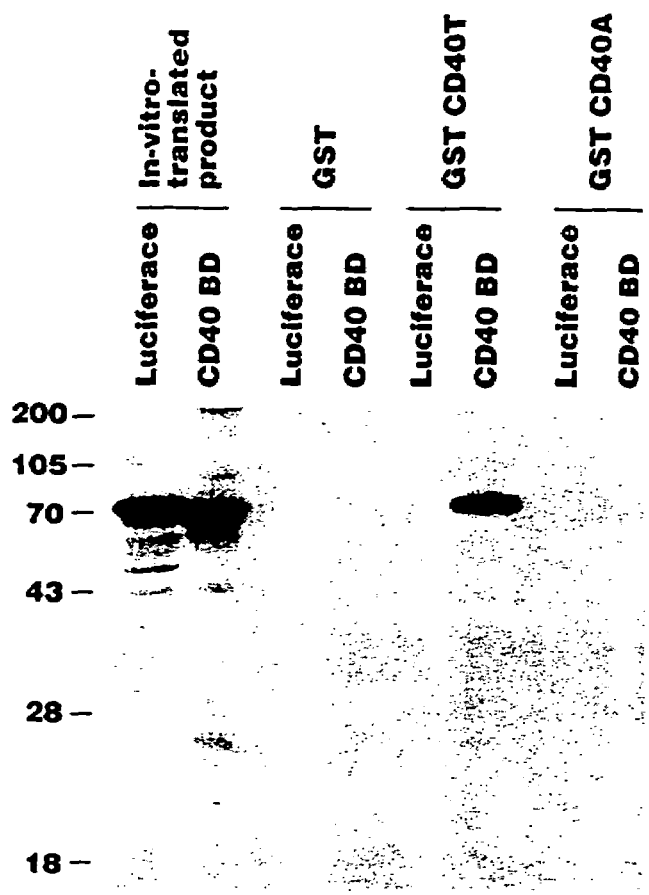
FIGS. 2A and 2B show the interaction of in vitro translated CD40bp with GST fusion proteins. [$^{35}$S]Methionine-labeled CD40bp or luciferase protein as control was incubated with GST alone, GSTCD40T (native CD40 cytoplasmic domain), or GSTCD40A (mutant CD40 cytoplasmic domain $Thr^{234} \rightarrow Ala$). Following incubation and washing, GST beads were boiled in SDS-sample buffer and resolved on a 10% acrylamide gel, and bound protein was visualized by autoradiography. The left panel shows the signal from 5 μl of labeled translated protein prior to incubation with GST beads.

To independently confirm the CD40-CD40bp interaction, the identical cytoplasmic domain regions of CD40 and mutant CD40 used in the yeast two-hybrid system were expressed as GST fusion proteins, immobilized to glutathione-agarose beads, and used to precipitate radiolabeled in vitro translated CD40bp. FIG. 2 shows in vitro translated CD40bp migrating with an apparent molecular mass of 64 kDa, which closely approximates the predicted molecular mass. CD40bp was effectively precipitated by native CD40 (GSTCD40T) but not by GST alone or, more significantly, by mutant CD40 (GSTCD40A). Furthermore, none of the GST proteins precipitated luciferase, a control for nonspecific binding. These studies further prove the specificity of the CD40-CD40bp interaction and implicate $Thr^{234}$ in the CD40 cytoplasmic domain as being fundamentally important in both signaling and CD40bp binding.

EXPERIMENT III

Construction of CD40 and CD40bp Expression Vectors—Full-length CD40 coding sequence was obtained by PCR from a human B-cell library (as described in Harper et al. (1993) supra) and confirmed by sequencing. The primers used were: CGGGGTACCGCCACCATGG-TTCGTCTGC-CTCTGCAG (SEQ ID NO: 10) for the upstream primer and TTTGTCGAC-TCACTGTCTCTCCTGCAC (SEQ ID NO: 11) for the downstream primer. The upstream primer had a built-in KpnI site and the downstream primer a SalI site (underlined) to facilitate cloning into the eukaryotic expression vector pcDNA3 (Invitrogen). Mutant CD40 (pCD40A) was made by site-directed mutagenesis using a two-step PCR protocol of Higuchi et al. (1988) *Nucleic Acids Res.* 16:7351-7367, and employing two additional oligonucleotides:

GCTCCAG-TGCAGGAAGCTTTACATGGATGC (SEQ ID NO: 12) and GCATCCATGTAAAGCTTCCTGCACTGG-AGC (altered bases are underlined). The Thr$^{234}$→Ala mutation in pCD40A was confirmed by sequence analysis.

To construct pHATagCD40bp, CD40bp was excised from the yeast vector pACT by XhoI digestion and subcloned into pcDNA3 in which an HA epitope tag (YPYDVPDYA) (SEQ ID NO: 14) had previously been placed downstream of the cytomegalovirus promoter/enhancer. The orientation of CD40bp and the junctional sequence between the HA tag and CD40bp were confirmed by sequence analysis.

Figure 3A:
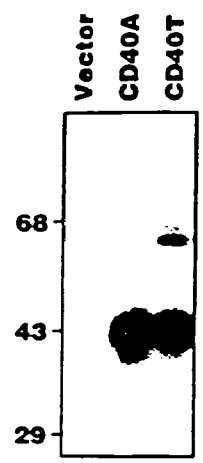
FIGS. 3A through 3E show the association of CD40 and CD40bp in vivo in transfected 293T and BJAB cells.
Figure 3B:
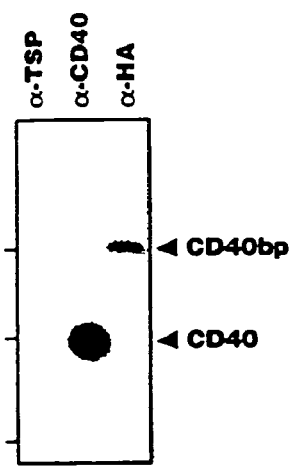

To demonstrate the interaction in vivo, 293T cells, a human epithelioid cell line available from the ATCC, (which is CD40-negative), were cotransfected with a HA epitope-tagged CD40bp expression construct and vector alone, mutant CD40 (CD40A), or native CD40 (CD40T) expression constructs. Following metabolic labeling with [$^{31}$S]methionine and [$^{35}$S]cysteine, cell lysates were subjected to an immunoprecipitation analysis with an anti-CD40 monoclonal antibody (FIG. 3A). No labeled protein was immunoprecipitated in vector-transfected cells, while, as expected, CD40 was immunoprecipitated in both CD40A and CD40T transfectant. However, only in cells transfected with native CD40 (CD40T) was there a co-precipitating protein whose molecular size corresponded to CD40bp. To confirm the identity of the precipitating proteins in the CD40T-transfected cells, the immune complex was dissociated and subjected to a second round of immunoprecipitation, as shown in FIG. 3B, with control anti-thrombospondin (α-TSP) antibody, anti-CD40 monoclonal antibody, or anti-HA epitope tag antibody (to identify HA-tagged CD40bp). While no labeled protein was precipitated by the control antibody, the anti-CD40 and anti-HA tag antibodies confirmed the presence of CD40 and CD40bp in the original immune complex.

EXPERIMENT IV

Transfection, Metabolic Cell Labeling, and Immunoprecipitation Analysis—These methods were performed essentially as described in O'Rourke et al. (1992) *J. Biol. Chem.* 267:24921-24924. For re-immunoprecipitation analysis, the initial immune complex was dissociated by boiling in PBS+1% SDS, diluted 10-fold in PBS containing 1% Triton X-100 and 1% deoxy-cholate, and subjected to a second round of immunoprecipitation analysis.

Figure 3C:
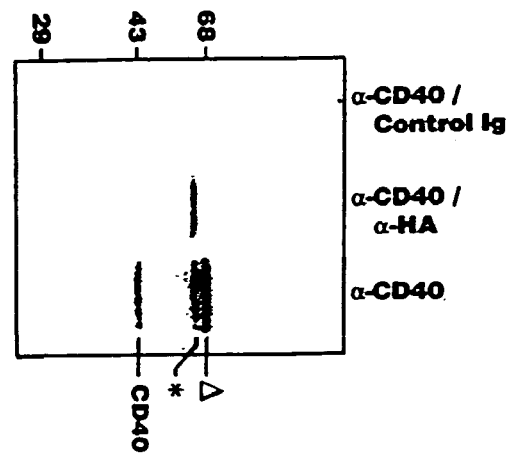
Figure 3D:
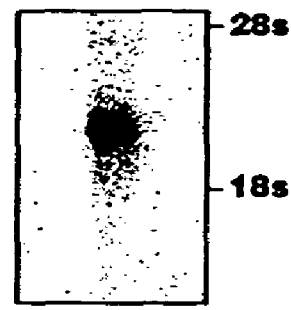
Figure 3E:
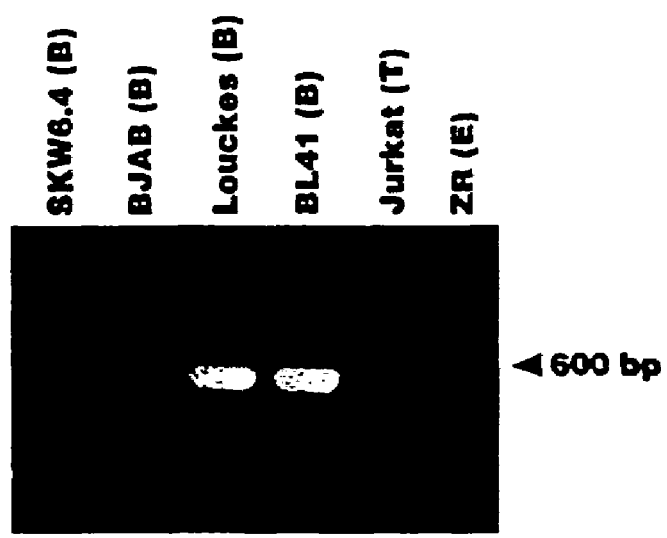

To conclusively show that CD40bp interacted with native CD40 in B-cells, the Epstein-Barr virus-negative, CD40-positive human B-cell line BJAB was transiently transfected with the epitope-tagged CD40bp expression construct and metabolically labeled, and endogenous. CD40 was immunoprecipitated with an anti-CD40 monoclonal antibody (FIG. 3C). Autoradiographic analysis of the precipitated proteins following SDS-polyacrylamide gel electrophoresis revealed, as expected, the presence of CD40 receptor but also that of two associated proteins, one that migrated just larger than CD40bp(Δ) and a fainter band that migrated at the expected molecular weight for CD40bp(*). To confirm that this was indeed CD40bp, the immune complex was dissociated and subjected to a second round of immunoprecipitation with either anti-HA epitope tag antibody or isotype-matched control antibody. CD40bp (corresponding to the band marked by an asterisk) was clearly immunoprecipitated by the anti-HA antibody and not by control antibody. This confirmed the presence of CD40bp in the original anti-CD40 immune complex and indicated that this insertion was capable of occurring in B-cells. Expression of CD40bp transcript in B-cell lines was confirmed by Northern blot and RT-PCR analysis (FIGS. 3D and 3E).

EXPERIMENT V

Transcript Analysis—mRNA analysis by Northern blotting and reverse transcriptase PCR ("RT-PCR") was performed as described previously in O'Rourke et al. (1992) supra using a commercially available kit from Perkin-Elmer. For the Northern blot, 7 μg of poly(A)$^+$ RNA from SKW6.4 cells was hybridized to a $^{32}$P-labeled CD40bp encoding XhoI fragment.

For RT-PCR, CD40bp-specific 18-mer oligonucleotide primers were used. The downstream primer (AGAGGAGT-TGCCTTCTGC) (SEQ ID NO: 15) was used initially for the reverse transcriptase reaction and later for PCR in conjunction with an upstream primer (GGCATGACCAGAT-GCTGA) (SEQ ID NO: 16) to give an expected size product of ~600 base pairs on agarose gel electrophoresis.

DNA Sequencing and Data Base Searching—Double stranded plasmid template was sequenced on both strands as described previously in O'Rourke et al. (1992) supra using modified T7 DNA polymerase. Initial data base homology searching revealed hundreds of matches to myosins and other α-helical, coiled-coil proteins. To further characterize portions of the CD40bp that might have coiled-coil potential, we used the COILS 2 program of Lupas et al. ((1991) *Science* 252:1162-1164), which has been updated recently (at lupas@ums.biochem.mpg.cle).

Figure 4D:
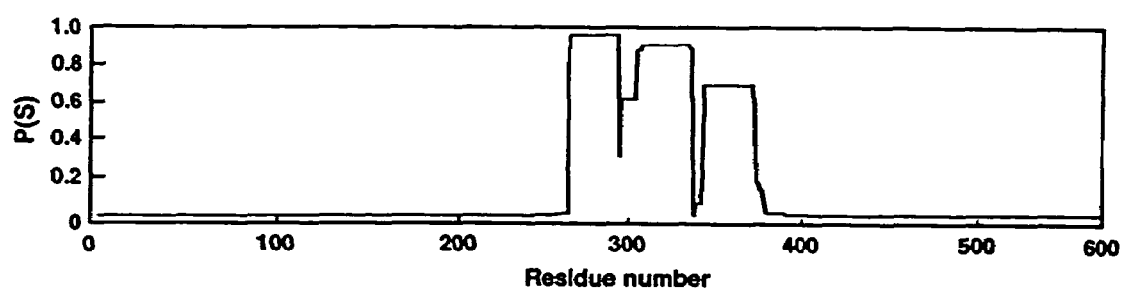

The deduced sequence of the 2350-base pair CD40bp cDNA revealed an open reading frame that began with an initiator methionine conforming to Kozak's consensus and that ended 567 residues later at an Opal codon. Given the presence of the open reading frame and the size of the CD40bp transcript (~2.5 kilobase pairs; FIG. 3D), it is likely that FIG. 4A represents the full-length coding sequence. Homology searching and use of the COILS algorithm revealed a discrete coiled-coil domain spanning residues 266-366 and flanked by regions without coiled-coil potential (FIG. 4D). Residues 266-366 of CD40bp were then "masked" by the method of Altschul et al. (1994) *Nature Genet.* 6:119-129, and the date base searches repeated. In this case there were 12 statistically significant (p<0.05) matches all to proteins known to contain the "RING finger" DNA-binding motif. Six of the 12 matches (including the most significant match) were to V(D)J recombination activating proteins (RAD1) from various species.

Importantly, one of the matches was the N-terminal RING finger sequence motif of TRAF2, which together with TRAF1, binds to the cytoplasmic domain of the 75-kDa TNF receptor as a heterodimeric complex in which TRAF2 contacts the receptor directly. The remaining matches included the human RING 1 gene product itself, the 52-kDA ribonucleoprotein autoantigen in Sjogren's syndrome, the *Neurospora* uvs-2 gene product thought to be involved in DNA repair, and a developmentally regulated *Dictyostelium* gene (DG17) of unknown function. The region between the RING finger and coiled-coil domains contains 17 cysteines and 10 histidines out of a total of 168 residues. These Cys/His residues are arranged in patterns resembling the "B box" motifs observed in some other RING finger proteins. Neither the RING finger or the coiled-coil segment, a motif known to mediate homo- and/or hetero-oligomerization appears necessary for binding to CD40 since one class of interacting CD40bp cDNAs identified in the two-hybrid screen encoded only the C-terminal half of CD40bp (beginning at Phe$^{297}$, which deletes the RING finger and truncates the coiled-coil segment). Instead, it appears likely that the C-terminal portion mediates CD40 binding.

This is supported by the finding that a similarly truncated TRAF2 protein (missing the RING finger domain) could still associate with the 75-kDA TNF receptor. In keeping with a common function for the C termini of these proteins is the remarkable sequence similarity that exists between the C-terminal half of CD40bp and the TRAF domains of TRAF1 and TRAF2 (FIG. 4E). Except for the RING finger domain in TRAF2, the three molecules are fairly distinct at their N-terminal halves. Taken together, these studies suggest that existence of a new family of proteins that associate with the cytoplasmic faces of the TNF receptor family and have in common the TRAF domain. Finally, given that TRAF1 and TRAF2 also possess central coiled-coil motifs, it will be important to determine if CD40bp can heterodimerize with these proteins.

Throughout this application, reference is made to various journal articles, U.S. patents and published applications. The disclosures of these references are hereby incorporated by reference into the present disclosure.

It is to be understood that while the invention has been described in conjunction with the above embodiments, that the foregoing description and the examples are intended to illustrate and not limit the scope of the invention. Other aspects, advantages and modifications within the scope of the invention will be apparent to those skilled in the art to which the invention pertains.

What is claimed is:

1. An isolated nucleic acid that encodes a polypeptide comprising the amino acid sequence shown in SEQ ID NO:2.

2. The isolated nucleic acid of claim 1, wherein the nucleic acid is cDNA or RNA.

3. A composition comprising the isolated nucleic acid of claim 1 and a carrier.

4. A vector comprising the isolated nucleic acid of claim 1.

5. An isolated host cell comprising the vector of claim 4.

6. A method of producing a mammalian protein or polypeptide having the ability to bind the cytoplasmic region of CD40 receptor, which comprises: a) growing the host cell of claim 5 under suitable conditions such that the nucleic acid is transcribed and translated into protein and b) purifying said protein.

* * * * *

SEQUENCE LISTING

```
<160> NUMBER OF SEQ ID NOS: 16

<210> SEQ ID NO 1
<211> LENGTH: 2339
<212> TYPE: DNA
<213> ORGANISM: Homo sapiens
<220> FEATURE:
<221> NAME/KEY: CDS
<222> LOCATION: (211)...(1911)

<400> SEQUENCE: 1
acgaaggcca cgcgcccggc gccctgagc cggccgagcg gcgacggacc gcgagatgag      60
gaaaatgagg cccaaagaag tgatgccact tggttaaggt cccagagcag gtcagaatca     120
gacctaggat cagaaacctg gctcctggct cctgctccct actcttctaa ggatcgctgt     180
cctgacagaa gagaactcct ctttcctaaa atg gag tcg agt aaa aag atg gac     234
                                    Met Glu Ser Ser Lys Lys Met Asp
                                      1               5 tct cct ggc gcg ctg cag act aac ccg ccg cta aag ctg cac act gac     282
Ser Pro Gly Ala Leu Gln Thr Asn Pro Pro Leu Lys Leu His Thr Asp
        10                  15                  20 cgc agt gct ggg acg cca gtt ttt gtc cct gaa caa gga ggt tac aag     330
Arg Ser Ala Gly Thr Pro Val Phe Val Pro Glu Gln Gly Gly Tyr Lys
 25                  30                  35                  40 gaa aag ttt gtg aag acc gtg gag gac aag tac aag tgt gag aag tgc     378
Glu Lys Phe Val Lys Thr Val Glu Asp Lys Tyr Lys Cys Glu Lys Cys
                     45                  50                  55 cac ctg gtg ctg tgc agc ccg aag cag acc gag tgt ggg cac cgc ttc     426
His Leu Val Leu Cys Ser Pro Lys Gln Thr Glu Cys Gly His Arg Phe
             60                  65                  70 tgc gag agc tgc atg gcg gcc ctg ctg agc tct tca agt cca aaa tgt     474
Cys Glu Ser Cys Met Ala Ala Leu Leu Ser Ser Ser Ser Pro Lys Cys
         75                  80                  85 aca gcg tgt caa gag agc atc gtt aaa gat aag gtg ttt aag gat aat     522
Thr Ala Cys Gln Glu Ser Ile Val Lys Asp Lys Val Phe Lys Asp Asn
     90                  95                 100 tgc tgc aag aga gaa att ctg gct ctt cag atc tat tgt cgg aat gaa     570
Cys Cys Lys Arg Glu Ile Leu Ala Leu Gln Ile Tyr Cys Arg Asn Glu
105                 110                 115                 120 agc aga ggt tgt gca gag cag tta atg ctg gga cat ctg gtg cat tta     618
Ser Arg Gly Cys Ala Glu Gln Leu Met Leu Gly His Leu Val His Leu
                125                 130                 135 aaa aat gat tgc cat ttt gaa gaa ctt cca tgt gtg cgt cct gac tgc     666
Lys Asn Asp Cys His Phe Glu Glu Leu Pro Cys Val Arg Pro Asp Cys
```

-continued

|  | 140 |  |  |  | 145 |  |  |  | 150 |  |  |  |  |
|---|---|---|---|---|---|---|---|---|---|---|---|---|---|
| aaa | gaa | aag | gtc | ttg | agg | aaa | gac | ctg | cga | gac | cac | gtg | gag | aag | gcg | 714 |
| Lys | Glu | Lys | Val | Leu | Arg | Lys | Asp | Leu | Arg | Asp | His | Val | Glu | Lys | Ala |  |
|  |  | 155 |  |  |  | 160 |  |  |  | 165 |  |  |  |  |  |  |

| tgt | aaa | tac | cgg | gaa | gcc | aca | tgc | agc | cac | tgc | aag | agt | cag | gtt | ccg | 762 |
| Cys | Lys | Tyr | Arg | Glu | Ala | Thr | Cys | Ser | His | Cys | Lys | Ser | Gln | Val | Pro |  |
| 170 |  |  |  |  | 175 |  |  |  |  | 180 |  |  |  |  |  |  |

| atg | atc | gcg | ctg | cag | aaa | cac | gaa | gac | acc | gac | tgt | ccc | tgc | gtg | gtg | 810 |
| Met | Ile | Ala | Leu | Gln | Lys | His | Glu | Asp | Thr | Asp | Cys | Pro | Cys | Val | Val |  |
| 185 |  |  |  |  | 190 |  |  |  |  | 195 |  |  |  |  | 200 |  |

| gtg | tcc | tgc | cct | cac | aag | tgc | agc | gtc | cag | act | ctc | ctg | agg | agc | gag | 858 |
| Val | Ser | Cys | Pro | His | Lys | Cys | Ser | Val | Gln | Thr | Leu | Leu | Arg | Ser | Glu |  |
|  |  |  |  | 205 |  |  |  |  | 210 |  |  |  |  | 215 |  |  |

| ttg | agt | gca | cac | ttg | tca | gag | tgt | gtc | aat | gcc | ccc | agc | acc | tgt | agt | 906 |
| Leu | Ser | Ala | His | Leu | Ser | Glu | Cys | Val | Asn | Ala | Pro | Ser | Thr | Cys | Ser |  |
|  |  |  |  | 220 |  |  |  |  | 225 |  |  |  |  | 230 |  |  |

| ttt | aag | cgc | tat | ggc | tgc | gtt | ttt | cag | ggg | aca | aac | cag | cag | atc | aag | 954 |
| Phe | Lys | Arg | Tyr | Gly | Cys | Val | Phe | Gln | Gly | Thr | Asn | Gln | Gln | Ile | Lys |  |
|  |  |  |  | 235 |  |  |  |  | 240 |  |  |  |  | 245 |  |  |

| gcc | cac | gag | gcc | agc | tcc | gcc | gtg | cag | cac | gtc | aac | ctg | ctg | aag | gag | 1002 |
| Ala | His | Glu | Ala | Ser | Ser | Ala | Val | Gln | His | Val | Asn | Leu | Leu | Lys | Glu |  |
|  | 250 |  |  |  |  | 255 |  |  |  |  | 260 |  |  |  |  |  |

| tgg | agc | aac | tcg | ctc | gaa | aag | aag | gtt | tcc | ttg | ttg | cag | aat | gaa | agt | 1050 |
| Trp | Ser | Asn | Ser | Leu | Glu | Lys | Lys | Val | Ser | Leu | Leu | Gln | Asn | Glu | Ser |  |
| 265 |  |  |  |  | 270 |  |  |  |  | 275 |  |  |  |  | 280 |  |

| gta | gaa | aaa | aac | aag | agc | ata | caa | agt | ttg | cac | aat | cag | ata | tgt | agc | 1098 |
| Val | Glu | Lys | Asn | Lys | Ser | Ile | Gln | Ser | Leu | His | Asn | Gln | Ile | Cys | Ser |  |
|  |  |  |  |  | 285 |  |  |  |  | 290 |  |  |  |  | 295 |  |

| ttt | gaa | att | gaa | att | gag | aga | caa | aag | gaa | atg | ctt | cga | aat | aat | gaa | 1146 |
| Phe | Glu | Ile | Glu | Ile | Glu | Arg | Gln | Lys | Glu | Met | Leu | Arg | Asn | Asn | Glu |  |
|  |  |  | 300 |  |  |  |  | 305 |  |  |  |  | 310 |  |  |  |

| tcc | aaa | atc | ctt | cat | tta | cag | cga | gtg | ata | gac | agc | caa | gca | gag | aaa | 1194 |
| Ser | Lys | Ile | Leu | His | Leu | Gln | Arg | Val | Ile | Asp | Ser | Gln | Ala | Glu | Lys |  |
|  |  | 315 |  |  |  |  | 320 |  |  |  |  | 325 |  |  |  |  |

| ctg | aag | gag | ctt | gac | aag | gag | atc | cgg | ccc | ttc | cgg | cag | aac | tgg | gag | 1242 |
| Leu | Lys | Glu | Leu | Asp | Lys | Glu | Ile | Arg | Pro | Phe | Arg | Gln | Asn | Trp | Glu |  |
|  | 330 |  |  |  |  | 335 |  |  |  |  | 340 |  |  |  |  |  |

| gaa | gca | gac | agc | atg | aag | agc | agc | gtg | gag | tcc | ctc | cag | aac | cgc | gtg | 1290 |
| Glu | Ala | Asp | Ser | Met | Lys | Ser | Ser | Val | Glu | Ser | Leu | Gln | Asn | Arg | Val |  |
| 345 |  |  |  |  | 350 |  |  |  |  | 355 |  |  |  |  | 360 |  |

| acc | gag | ctg | gag | agc | gtg | gac | aag | agc | gcg | ggg | caa | gtg | gct | cgg | aac | 1338 |
| Thr | Glu | Leu | Glu | Ser | Val | Asp | Lys | Ser | Ala | Gly | Gln | Val | Ala | Arg | Asn |  |
|  |  |  |  | 365 |  |  |  |  | 370 |  |  |  |  | 375 |  |  |

| aca | ggc | ctg | ctg | gag | tcc | cag | ctg | agc | cgg | cat | gac | cag | atg | ctg | agt | 1386 |
| Thr | Gly | Leu | Leu | Glu | Ser | Gln | Leu | Ser | Arg | His | Asp | Gln | Met | Leu | Ser |  |
|  |  |  | 380 |  |  |  |  | 385 |  |  |  |  | 390 |  |  |  |

| gtg | cac | gac | atc | cgc | cta | gcc | gac | atg | gac | ctg | ggc | ttc | cag | gtc | ctg | 1434 |
| Val | His | Asp | Ile | Arg | Leu | Ala | Asp | Met | Asp | Leu | Gly | Phe | Gln | Val | Leu |  |
|  |  | 395 |  |  |  |  | 400 |  |  |  |  | 405 |  |  |  |  |

| gag | acc | gcc | agc | tac | aat | gga | gtg | ctc | atc | tgg | aag | att | cgc | gac | tac | 1482 |
| Glu | Thr | Ala | Ser | Tyr | Asn | Gly | Val | Leu | Ile | Trp | Lys | Ile | Arg | Asp | Tyr |  |
|  | 410 |  |  |  |  | 415 |  |  |  |  | 420 |  |  |  |  |  |

| aag | cgg | cgg | aag | cag | gag | gcc | gtc | atg | ggg | aag | acc | ctg | tcc | ctt | tac | 1530 |
| Lys | Arg | Arg | Lys | Gln | Glu | Ala | Val | Met | Gly | Lys | Thr | Leu | Ser | Leu | Tyr |  |
| 425 |  |  |  |  | 430 |  |  |  |  | 435 |  |  |  |  | 440 |  |

| agc | cag | cct | ttc | tac | act | ggt | tac | ttt | ggc | tat | aag | atg | tgt | gcc | agg | 1578 |
| Ser | Gln | Pro | Phe | Tyr | Thr | Gly | Tyr | Phe | Gly | Tyr | Lys | Met | Cys | Ala | Arg |  |
|  |  |  |  | 445 |  |  |  |  | 450 |  |  |  |  | 455 |  |  |

| gtc | tac | ctg | aac | ggg | gac | ggg | atg | ggg | aag | ggg | acg | cac | ttg | tcg | ctg | 1626 |

-continued

```
Val Tyr Leu Asn Gly Asp Gly Met Gly Lys Gly Thr His Leu Ser Leu
            460                 465                 470 ttt ttt gtc atc atg cgt gga gaa tat gat gcc ctg ctt cct tgg ccg    1674
Phe Phe Val Ile Met Arg Gly Glu Tyr Asp Ala Leu Leu Pro Trp Pro
            475                 480                 485 ttt aag cag aaa gtg aca ctc atg ctg atg gat cag ggg tcc tct cga    1722
Phe Lys Gln Lys Val Thr Leu Met Leu Met Asp Gln Gly Ser Ser Arg
            490                 495                 500 cgt cat ttg gga gat gca ttc aag ccc gac ccc aac agc agc agc ttc    1770
Arg His Leu Gly Asp Ala Phe Lys Pro Asp Pro Asn Ser Ser Ser Phe
505                 510                 515                 520 aag aag ccc act gga gag atg aat atc gcc tct ggc tgc cca gtc ttt    1818
Lys Lys Pro Thr Gly Glu Met Asn Ile Ala Ser Gly Cys Pro Val Phe
                525                 530                 535 gtg gcc caa act gtt cta gaa aat ggg aca tat att aaa gat gat aca    1866
Val Ala Gln Thr Val Leu Glu Asn Gly Thr Tyr Ile Lys Asp Asp Thr
            540                 545                 550 att ttt att aaa gtc ata gtg gat act tcg gat ctg ccc gat ccc        1911
Ile Phe Ile Lys Val Ile Val Asp Thr Ser Asp Leu Pro Asp Pro
            555                 560                 565 tgataagtag ctggggaggt ggatttagca gaaggcaact cctctggggg atttgaaccg   1971
gtctgtcttc actgaggtcc tcgcgctcag aaaaggacct tgtgagacgg aggaagcggc   2031
agaaggcgga cgcgtgccgg cgggaggagc cacgcgagag cacacctgac acgttttata   2091
atagactagc cacacttcac tctgaagaat tatttatcct tcaacaagat aaatattgct   2151
gtcagagaag gttttcattt tcatttttaa agatctagtt aattaaggtg gaaaacatat   2211
atgctaaaca aaagaaacat gattttttctt ccttaaactt gaacaccaaa aaaacacaca   2271
cacacacaca cgtggggata gctggacatg tcagcatgtt aagtaaaagg agaatttatg   2331
aaatagta                                                            2339
```

```
<210> SEQ ID NO 2
<211> LENGTH: 567
<212> TYPE: PRT
<213> ORGANISM: Homo sapiens

<400> SEQUENCE: 2

Met Glu Ser Ser Lys Lys Met Asp Ser Pro Gly Ala Leu Gln Thr Asn
1               5                   10                  15

Pro Pro Leu Lys Leu His Thr Asp Arg Ser Ala Gly Thr Pro Val Phe
            20                  25                  30

Val Pro Glu Gln Gly Gly Tyr Lys Glu Lys Phe Val Lys Thr Val Glu
        35                  40                  45

Asp Lys Tyr Lys Cys Glu Lys Cys His Leu Val Leu Cys Ser Pro Lys
    50                  55                  60

Gln Thr Glu Cys Gly His Arg Phe Cys Glu Ser Cys Met Ala Ala Leu
65                  70                  75                  80

Leu Ser Ser Ser Ser Pro Lys Cys Thr Ala Cys Gln Glu Ser Ile Val
                85                  90                  95

Lys Asp Lys Val Phe Lys Asp Asn Cys Cys Lys Arg Glu Ile Leu Ala
            100                 105                 110

Leu Gln Ile Tyr Cys Arg Asn Glu Ser Arg Gly Cys Ala Glu Gln Leu
        115                 120                 125

Met Leu Gly His Leu Val His Leu Lys Asn Asp Cys His Phe Glu Glu
    130                 135                 140

Leu Pro Cys Val Arg Pro Asp Cys Lys Glu Lys Val Leu Arg Lys Asp
```

-continued

```
            145                 150                 155                 160
Leu Arg Asp His Val Glu Lys Ala Cys Lys Tyr Arg Glu Ala Thr Cys
                    165                 170                 175
Ser His Cys Lys Ser Gln Val Pro Met Ile Ala Leu Gln Lys His Glu
                    180                 185                 190
Asp Thr Asp Cys Pro Cys Val Val Ser Cys Pro His Lys Cys Ser
            195                 200                 205
Val Gln Thr Leu Leu Arg Ser Glu Leu Ser Ala His Leu Ser Glu Cys
            210                 215                 220
Val Asn Ala Pro Ser Thr Cys Ser Phe Lys Arg Tyr Gly Cys Val Phe
225                 230                 235                 240
Gln Gly Thr Asn Gln Gln Ile Lys Ala His Glu Ala Ser Ser Ala Val
                    245                 250                 255
Gln His Val Asn Leu Leu Lys Glu Trp Ser Asn Ser Leu Glu Lys Lys
                260                 265                 270
Val Ser Leu Leu Gln Asn Glu Ser Val Glu Lys Asn Lys Ser Ile Gln
            275                 280                 285
Ser Leu His Asn Gln Ile Cys Ser Phe Glu Ile Glu Ile Glu Arg Gln
            290                 295                 300
Lys Glu Met Leu Arg Asn Asn Glu Ser Lys Ile Leu His Leu Gln Arg
305                 310                 315                 320
Val Ile Asp Ser Gln Ala Glu Lys Leu Lys Glu Leu Asp Lys Glu Ile
                    325                 330                 335
Arg Pro Phe Arg Gln Asn Trp Glu Glu Ala Asp Ser Met Lys Ser Ser
                340                 345                 350
Val Glu Ser Leu Gln Asn Arg Val Thr Glu Leu Glu Ser Val Asp Lys
                355                 360                 365
Ser Ala Gly Gln Val Ala Arg Asn Thr Gly Leu Leu Glu Ser Gln Leu
            370                 375                 380
Ser Arg His Asp Gln Met Leu Ser Val His Asp Ile Arg Leu Ala Asp
385                 390                 395                 400
Met Asp Leu Gly Phe Gln Val Leu Glu Thr Ala Ser Tyr Asn Gly Val
                    405                 410                 415
Leu Ile Trp Lys Ile Arg Asp Tyr Lys Arg Arg Lys Gln Glu Ala Val
                420                 425                 430
Met Gly Lys Thr Leu Ser Leu Tyr Ser Gln Pro Phe Tyr Thr Gly Tyr
                435                 440                 445
Phe Gly Tyr Lys Met Cys Ala Arg Val Tyr Leu Asn Gly Asp Gly Met
            450                 455                 460
Gly Lys Gly Thr His Leu Ser Leu Phe Phe Val Ile Met Arg Gly Glu
465                 470                 475                 480
Tyr Asp Ala Leu Leu Pro Trp Pro Phe Lys Gln Lys Val Thr Leu Met
                    485                 490                 495
Leu Met Asp Gln Gly Ser Ser Arg Arg His Leu Gly Asp Ala Phe Lys
                500                 505                 510
Pro Asp Pro Asn Ser Ser Phe Lys Lys Pro Thr Gly Glu Met Asn
                515                 520                 525
Ile Ala Ser Gly Cys Pro Val Phe Val Ala Gln Thr Val Leu Glu Asn
            530                 535                 540
Gly Thr Tyr Ile Lys Asp Asp Thr Ile Phe Ile Lys Val Ile Val Asp
545                 550                 555                 560
Thr Ser Asp Leu Pro Asp Pro
                565
```

<210> SEQ ID NO 3
<211> LENGTH: 49
<212> TYPE: PRT
<213> ORGANISM: Homo sapiens

<400> SEQUENCE: 3

Asp Lys Tyr Lys Cys Glu Lys Cys His Leu Val Leu Cys Ser Pro Lys
 1               5                  10                  15

Gln Thr Glu Cys Gly His Arg Phe Cys Glu Ser Cys Met Ala Ala Leu
            20                  25                  30

Leu Ser Ser Ser Ser Pro Lys Cys Thr Ala Cys Gln Glu Ser Ile Val
        35                  40                  45

Lys

<210> SEQ ID NO 4
<211> LENGTH: 50
<212> TYPE: PRT
<213> ORGANISM: Homo sapiens

<400> SEQUENCE: 4

Ala Lys Tyr Leu Cys Ser Ala Cys Lys Asn Ile Leu Arg Arg Pro Phe
 1               5                  10                  15

Gln Ala Gln Cys Gly His Arg Tyr Cys Ser Phe Cys Leu Thr Ser Ile
            20                  25                  30

Leu Ser Ser Gly Pro Gln Asn Cys Ala Ala Cys Val Tyr Glu Gly Leu
        35                  40                  45

Tyr Glu
    50

<210> SEQ ID NO 5
<211> LENGTH: 49
<212> TYPE: PRT
<213> ORGANISM: Homo sapiens

<400> SEQUENCE: 5

Lys Ser Ile Ser Cys Gln Ile Cys Glu His Ile Leu Ala Asp Pro Val
 1               5                  10                  15

Glu Thr Asn Cys Lys His Val Phe Cys Arg Val Cys Ile Leu Arg Cys
            20                  25                  30

Leu Lys Val Met Gly Ser Tyr Cys Pro Ser Cys Arg Tyr Pro Cys Phe
        35                  40                  45

Pro

<210> SEQ ID NO 6
<211> LENGTH: 50
<212> TYPE: PRT
<213> ORGANISM: Homo sapiens

<400> SEQUENCE: 6

Ser Glu Leu Met Cys Pro Ile Cys Leu Asp Met Leu Lys Asn Thr Met
 1               5                  10                  15

Thr Thr Lys Glu Cys Leu His Arg Phe Cys Ser Asp Cys Ile Val Thr
            20                  25                  30

Ala Leu Arg Ser Gly Asn Lys Glu Cys Pro Thr Cys Arg Lys Lys Leu
        35                  40                  45

Val Ser
    50

```
<210> SEQ ID NO 7
<211> LENGTH: 49
<212> TYPE: PRT
<213> ORGANISM: Homo sapiens

<400> SEQUENCE: 7

Glu Glu Val Thr Cys Pro Ile Cys Leu Asp Pro Phe Val Glu Pro Val
 1               5                  10                  15

Ser Ile Glu Cys Gly His Ser Phe Cys Gln Glu Cys Ile Ser Gln Val
            20                  25                  30

Gly Lys Gly Gly Gly Ser Val Cys Pro Val Cys Arg Gln Arg Phe Leu
        35                  40                  45

Leu

<210> SEQ ID NO 8
<211> LENGTH: 48
<212> TYPE: PRT
<213> ORGANISM: Homo sapiens

<400> SEQUENCE: 8

Gln Ala Phe Arg Cys His Val Cys Lys Asp Phe Tyr Asp Ser Pro Met
 1               5                  10                  15

Leu Thr Ser Cys Asn His Thr Phe Cys Ser Leu Cys Ile Arg Arg Cys
            20                  25                  30

Leu Ser Val Asp Ser Lys Cys Pro Leu Cys Arg Ala Thr Asp Gln Glu
        35                  40                  45

<210> SEQ ID NO 9
<211> LENGTH: 50
<212> TYPE: PRT
<213> ORGANISM: Homo sapiens

<400> SEQUENCE: 9

Asn Lys Tyr Thr Cys Pro Ile Cys Phe Glu Phe Ile Tyr Lys Lys Gln
 1               5                  10                  15

Ile Tyr Gln Cys Lys Ser Gly His His Ala Cys Lys Glu Cys Trp Glu
            20                  25                  30

Lys Ser Leu Glu Thr Lys Lys Glu Cys Met Thr Cys Lys Ser Val Val
        35                  40                  45

Asn Ser
    50

<210> SEQ ID NO 10
<211> LENGTH: 36
<212> TYPE: DNA
<213> ORGANISM: Homo sapiens

<400> SEQUENCE: 10
cggggtaccg ccaccatggt tcgtctgcct ctgcag                          36

<210> SEQ ID NO 11
<211> LENGTH: 27
<212> TYPE: DNA
<213> ORGANISM: Homo sapiens

<400> SEQUENCE: 11
tttgtcgact cactgtctct cctgcac                                    27

<210> SEQ ID NO 12
<211> LENGTH: 30
```

```
<212> TYPE: DNA
<213> ORGANISM: Homo sapiens

<400> SEQUENCE: 12
gctccagtgc aggaagcttt acatggatgc                                             30

<210> SEQ ID NO 13
<211> LENGTH: 30
<212> TYPE: DNA
<213> ORGANISM: Homo sapiens

<400> SEQUENCE: 13
gcatccatgt aaagcttcct gcactggagc                                             30

<210> SEQ ID NO 14
<211> LENGTH: 9
<212> TYPE: PRT
<213> ORGANISM: Homo sapiens

<400> SEQUENCE: 14

Tyr Pro Tyr Asp Val Pro Asp Tyr Ala
  1               5

<210> SEQ ID NO 15
<211> LENGTH: 18
<212> TYPE: DNA
<213> ORGANISM: Homo sapiens

<400> SEQUENCE: 15
agaggagttg ccttctgc                                                          18

<210> SEQ ID NO 16
<211> LENGTH: 18
<212> TYPE: DNA
<213> ORGANISM: Homo sapiens

<400> SEQUENCE: 16
ggcatgacca gatgctga                                                          18
```